United States Patent [19]

White et al.

[11] Patent Number: 4,609,447

[45] Date of Patent: Sep. 2, 1986

[54] METHOD OF DETECTING ALKALI METAL IONS

[75] Inventors: Lawrence K. White, W. Windsor Township, Mercer County; Jen-shen Maa, Plainsboro Township, Mercer County, both of N.J.

[73] Assignee: RCA Corporation, Princeton, N.J.

[21] Appl. No.: 693,353

[22] Filed: Jan. 22, 1985

[51] Int. Cl.$^4$ .......................................... H01L 21/306
[52] U.S. Cl. .................. 204/192 E; 156/626; 156/643; 156/662
[58] Field of Search .............. 204/192 E; 156/626, 156/643, 662

[56] References Cited

U.S. PATENT DOCUMENTS 4,289,573  9/1981  Economy et al. ................. 156/643
4,512,847  4/1985  Brunsch et al. .................... 156/626

OTHER PUBLICATIONS

Makino et al., J. Elect. Chemical Society, vol. 128, No. 1, pp. 103–106, 1981.

*Primary Examiner*—John F. Niebling
*Assistant Examiner*—William T. Leader
*Attorney, Agent, or Firm*—B. E. Morris; R. Hain Swope

[57] ABSTRACT

A method of determining the presence of alkali metal ions in a substrate comprising silicon or silicon doped with a p-type conductivity modifier is provided. The substrate to be tested is etched in a tetrafluoromethane/oxygen plasma and the etch rate is compared against that of similar substrates containing known concentrations of alkali metal ions. The etch rate will increase with increasing alkali metal concentration. The subject method is particularly useful in determining the level of alkali metal ion contamination during multistep processing of the above-named substrates.

7 Claims, No Drawings

METHOD OF DETECTING ALKALI METAL IONS

This invention relates to a method of detecting the presence of undesirable alkali metal ions in silicon materials.

BACKGROUND OF THE INVENTION

The presence of alkali metal ions, particularly sodium ions, is detrimental to the functioning of metal-on-silicon (MOS) devices. Alkali metal ions diffuse rapidly, particularly through silicon dioxide. Sodium ions, for example, are mobile in silicon dioxide even at room temperature. Because they carry an electric (positive) charge, the presence of alkali metal ions will cause the electrical characteristics of a device to drift, with a potentially substantial loss of control of critical functions. Typically, a significant concentration of contaminating alkali metal ions will change the surface potential of an insulator such silicon dioxide resulting in a material loss of stability of the device.

It is recognized that, as a practical matter, it is impossible to completely eliminate alkali metal ion contamination from a device or structure. Such contamination may be minimized to a degree, however, by incorporating into the device or structure certain materials, such as phosphosilicate glass, which getter or chelate alkali metal ions. Such materials, however, are only effective in removing limited amounts of alkali metal ion contaminants. As it is very difficult to remove these contaminants, it will be appreciated that a method of conveniently detecting the presence of unacceptably high concentrations thereof at an early stage in device manufacture is of considerable advantage in saving expensive, time-consuming processing operations. Such a method is provided in accordance with this invention.

SUMMARY OF THE INVENTION

The presence of alkali metal ions in a silicon structure is determined by comparing the plasma etch rate of the structure in a particular plasma with that of a similar structure of known alkali metal ion concentration.

DETAILED DESCRIPTION OF THE INVENTION

The method of this invention is useful in determining substantial contamination of a silicon substrate, e.g. a silicon wafer, by alkali metal ions, e.g. sodium, potassium, lithium or cesium ions. Sodium ions followed by potassium ions, are of the greatest concern in semiconductor processing since they are a frequent contaminant of silicon substrates. Further, due to their small mass, sodium ions migrate most readily and, therefore, can produce the greatest damage to a silicon device in terms of drift and loss of control.

The method of this invention utilizes, as a point of reference, substrates comprised of silicon or silicon doped with a p-type conductivity modifier such as boron. The silicon can be single crystalline or polycrystalline material. When a p-type conductivity modified is desired, a layer of doped silicon can be conventionally deposited onto a suitable substrate, or the surface portion of a silicon wafer or a silicon layer may be doped by conventional techniques such as diffusion, ion-implantation and the like. It is, of course, necessary that the surface layer of the reference substrates be of the same material as that of a substrate containing an unknown amount of alkali metal ion contamination which is being tested in accordance with the present method. The present method is ineffective if the contaminant is an ion other than an alkali metal ion, or if the substrate is silicon nitride, tantalum silicide, or silicon doped with an n-type conductivity modifier such as phosphorus.

The diagnostic method of this invention is based on the fact that silicon substrates containing alkali metal ions will etch at a substantially increased rate in a plasma of tetrafluoromethane and oxygen than substrates that are free of alkali metal ions. Further, the amount of increase in the etch rate is an indication of the level of alkali metal ion contamination.

The etch mixture utilized in the subject detection method comprises from about 99 to 70, preferably about 95, percent by volume of tetrafluoromethane and from about 1 to 30, preferably about 5, percent by volume of oxygen. The plasma etching of the unknown and reference substrates is carried out under conventional conditions utilizing conventional apparatus.

Etching is advantageously carried out on a plurality of reference substrates having known levels of alkali metal ion contamination to ascertain the degree of contamination in the unknown substrate. However, a single reference substrate having a level of contamination regarded as the maximum that can be tolerated in a given device can also be used for a rapid and convenient means of determining at any point during a device fabrication whether the level of contamination has become unacceptably high. This represents a significant cost savings in terms of processing that would otherwise be continued on unacceptable substrates.

A particular point in the processing of a semiconductor substrate where the detection method of this invention is advantageous is following wet chemical development of a positive photoresist. Frequently, the developing solutions for positive photoresists contain alkali metal ions which can enter the substrate during development of the resist pattern. Even repeated rinsing of the substrate is, for the most part, ineffective in removing such contamination. The resulting alkali metal ion contamination, which is nonuniform, produces a correspondingly nonuniform etch of open areas of the underlying silicon substrate, causes excessive undercutting and the like.

The increase in the etch rate of silicon or p-type silicon doped with a p-type conductivity modifer such as boron varies from about 20 percent up to about ten fold. The exact mechanism responsible for this phenomenon is not known with certainty. In order for the subject method to be effective, the etch mixture must be free of chlorine as its presence has been found to negate the etch acceleration. For example, no etch acceleration will be observed utilizing a chlorotrifluoromethane plasma. The reason for this phenomenon is likewise not understood with certainty.

The comparison of etch rates of an unknown substrate with one or more reference substrates in accordance with this invention can be carried out in a variety of ways as will be appreciated by those of ordinary skill in the art. Preferably, etching is carried out for a predetermined time, e.g. one minute, in a conventional plasma reactor and the amount of substrate removed in each instance measured by conventional means, such as profilometric etch depth or interoferometric etch rate monitors. When unknown substrates are withdrawn from a manufacturing process for testing, it is preferable to test a number of such substrates because alkali metal ion contamination is frequently nonuniform.

As an alternative, specially constructed reference substrates may be processed with the unknown substrates and utilized for the subject determination. Such substrates are layered structures having a surface layer of silicon or silicon doped with a p-type conductivity modifier overlying an indicator layer which provides a means of indicating that etching of the silicon layer is complete, for example, by a change wherein etching of the silicon layer is being monitored by emission spectroscopy. The indicator layer may also be comprised of or contain a material which becomes detectable, e.g. has a detectable emission spectrum, upon contact with the subject plasma. Such a material may, for example, form a volatile reaction product detectable in the reaction chamber itself or in the effluent, e.g. by optical or mass spectroscopic analysis. Such materials are known to those skilled in the art. The etch time until the indicator material is detected is utilized to calculate the etch rates of the references substrates and, therefore, the unknown substrates.

With regard to the manufacture of devices such as VLSI circuits, the subject method provides a basis for deciding at intermediate points in a multistep processing sequence whether the processing should be discontinued and the substrate discarded or reworked because the finished devices will not be acceptable due to undesirable levels of alkali metal ions. The economic benefits realized from being able to accurately make such a determination are substantial.

The following Examples further illustrate this invention, it being understood that the invention is in no way intended to be limited to the details described therein. In the Examples, all parts and percentages are on a weight basis and all temperatures are in degrees Celsius, unless otherwise stated.

EXAMPLE 1

Three inch silicon wafers were immersed in a series of test solutions. Groups of 5 wafers were immersed for one minute in 0.5 molar aqueous solutions of sodium hydroxide, sodium chloride, potassium hydroxide, calcium chloride and tetramethylammonium hydroxide, respectively. The wafers were etched in a conventional parallel plate reactor at 0.1 torr in a plasma consisting of 95 percent by volume of tetrafluoromethane and 5 percent by volume of oxygen. The etch rates of the test wafers were compared to etch rates for similar wafers which had not been exposed to a test contaminant solution.

It was observed that the etch rates for the wafers exposed to calcium chloride and tetramethylammonium hydroxide were the same as the untreated wafers. Each of the wafers treated with alkali metal ion, i.e., sodium hydroxide, sodium chloride and potassium hydroxide, etched at a rate at least 50 percent higher than the untreated wafers.

Similar wafers were coated with a one micrometer thick layer of phosphosilicate glass containing three percent of phosphorus and a 0.5 micrometer thick layer of silicon nitride, respectively, by conventional chemical vapor deposition, and with a 0.2 micrometer thick layer of tantalum silicide by conventional sputtering. Each of these wafers were exposed to sodium hydroxide as above. None of these wafers showed any increase in etch rate in comparison with wafers having the same coatings, but not exposed to the sodium hydroxide solution.

A final wafer was exposed to sodium hydroxide solution and etched under the same conditions in a chlorotrifluoromethane plasma. No increase in etch rate was observed in comparison to an unexposed wafer which had been etched in the same plasma.

EXAMPLE 2

A total of four three-inch silicon wafers were coated with a one-micrometer thick coating of the positive photoresist HPR 204, Hunt Chemical Co. and flood irradiated with a high intensity mercury lamp. The wafers were then immersed in the aqueous developer LSI, Type I, Hunt Chemical Co. for one minute. The wafers were withdrawn and rinsed three times with deionized water.

The wafers were placed into a conventional parallel plate reactor and etched in a tetrafluoromethane/oxygen plasma as described in Example 1. The etch rate of the wafers which had been immersed in the developer solution was, on the average, twice the etch rate of wafers which were not exposed to the developer solution. The sensitivity and advantage of the subject method are clearly demonstated by these results.

We claim:

1. A method of determining the presence of alkali metal ions in a substrate consisting of silicon or silicon doped with a p-type conductivity modifier which comprises:
    (a) providing one or more reference substrates of the same material as said substrate and having a known alkali metal ion concentration;
    (b) plasma etching said substrates in a plasma comprising tetrafluoromethane and oxygen; and
    (c) comparing the etch rates of said substrates.

2. A method in accordance with claim 1, wherein the p-type conductivity modifier is boron.

3. A method in accordance with claim 1, wherein the alkali metal ion contaminant is sodium ions.

4. A method in accordance with claim 1, wherein the plasma comprises, on a volume basis, from about 99 to about 70 percent of tetrafluoromethane and from about 1 to about 30 percent of oxygen.

5. A method in accordance with claim 4, wherein the plasma comprses about 95 percent by volume of tetrafluoromethane and about 5 percent by volume of oxygen.

6. A method in accordance with claim 1, wherein the substrates having a known alkali metal ion concentration comprise a surface layer of silicon or silicon doped with a p-type conductivity modifier, said layer overlying a layer which provides an indication that etching of said silicon layer is complete.

7. A method in accordance with claim 6, wherein the indicator layer comprises a material which becomes detectable upon contact with said plasma.

* * * * *